| United States Patent [19]
Somkuti et al.

[11] Patent Number: 5,071,763
[45] Date of Patent: Dec. 10, 1991

[54] LACTOSE HYDROLYSIS BY MUTANT STREPTOCOCCUS THERMOPHILUS

[75] Inventors: George A. Somkuti, Lansdale; Dennis H. Steinberg, Philadelphia, both of Pa.

[73] Assignee: The United States of America as represented by the Secretary of Agriculture, Washington, D.C.

[21] Appl. No.: 513,480

[22] Filed: Apr. 23, 1990

[51] Int. Cl.[5] .......................... C12R 1/46; C12P 19/14
[52] U.S. Cl. .................................. 435/253.4; 435/99; 435/252.3; 435/885
[58] Field of Search .................... 435/99, 252.3, 253.4, 435/885

[56] References Cited

PUBLICATIONS

Derwent Biochem Abs 86-08756 Herman et al., J. Dairy Sci (1986) 69 #Suppl. 1, 69D59.
Derwent Biochem Abs 84-08991 Thomas et al., Appl. Environ. Microbiol. (1984), 48, 1, 186-91.
Derwent Biochem Abs. 89-10297 Mercenier et al., Abs. Annu. Am. Soc. Microbiol. (1989), 89 Meet. 310.
Derwent Biochem. Abs. 90-06366 Beal et al., Appl. Microbiol. Biotech. (1989), 32, 2, 148-54.
Derwent WPIL Abs. 89-194499/27 Kobayashi et al., EP-323201 (7-1989).
Derwent WPIL Abs. 82-00768E/01 Mitsubishi Chem. J56154991 (11-1981).
Derwent Biotech Abs. 81-154991 Fukuda J56154991 (Nov. 1981).

*Primary Examiner*—Herbert J. Lilling
*Attorney, Agent, or Firm*—M. Howard Silverstein; John D. Fado; Joseph A. Lipovsky

[57] ABSTRACT

Mutant strains of *Streptococcus thermophilus* having defective lactose transport systems having a phenotype gluS$^{31}$, lacS$^-$, sucS$^+$ and $\beta$gal$^+$ are effective for use in processes where the hydrolysis of lactose is sought. Thermostability of these strains as well as the $\beta$-galactosidase produced allows lactose hydrolysis prior to and during pasteurization. These organisms provide the food industry with improved methods of making reduced lactose dairy products.

3 Claims, 2 Drawing Sheets

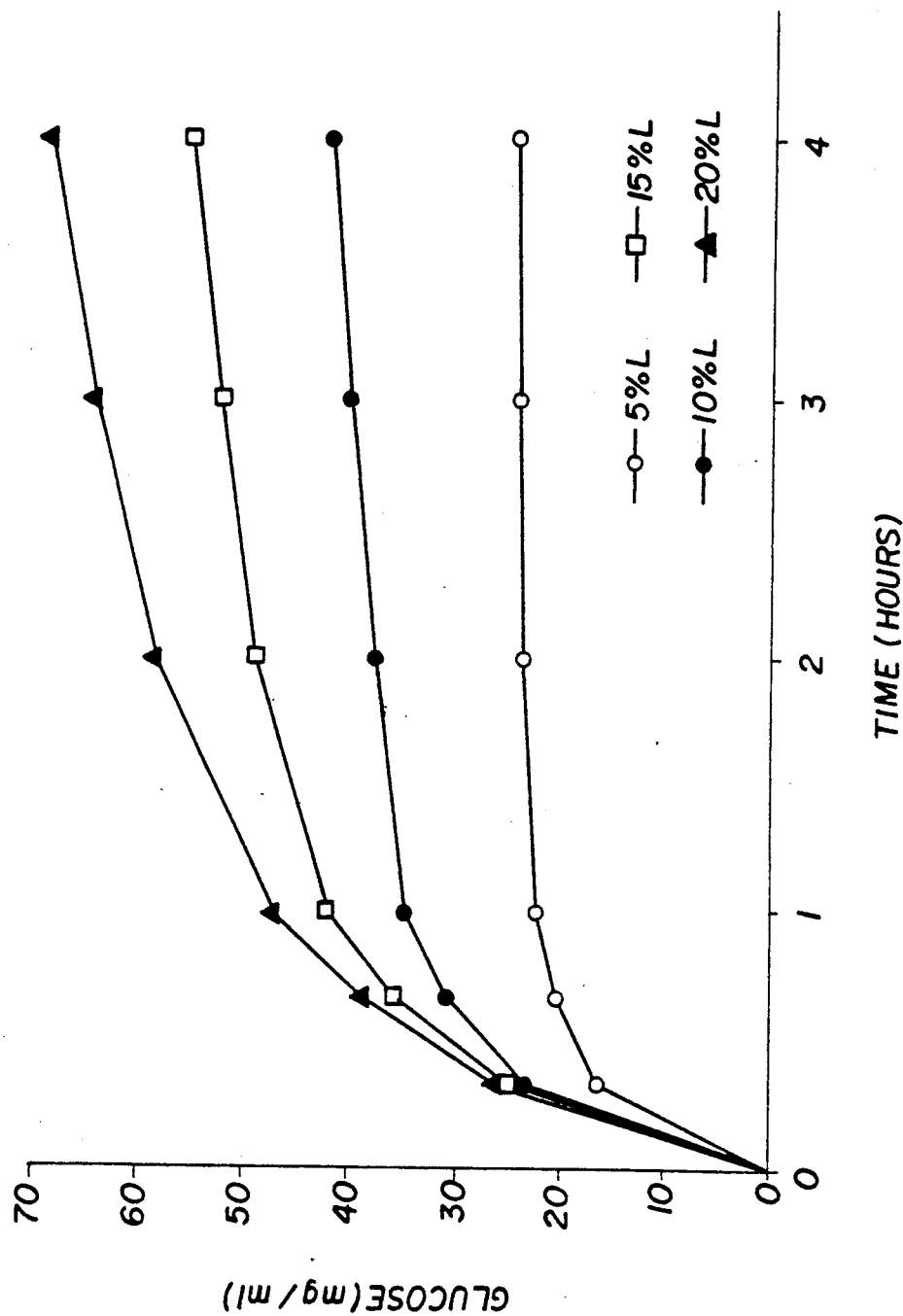

LACTOSE HYDROLYSIS BY MUTANT STREPTOCOCCUS THERMOPHILUS

BACKGROUND OF THE INVENTION

1. Field of the Invention

The present invention relates to a mutant strain of *Streptococcus thermophilus* having a defective lactose transport system. The organism has utility in food and commercial applications where a reduction of lactose is sought.

2. Description of the Prior Art

β-galactosidase (β-D-galactoside galactohydrolase, EC 3.2.1.23) hydrolyzes lactose to its hexose components, glucose, and galactose. β-galactosidase is used commercially primarily in the food industry to eliminate lactose from dairy products. In a large segment of the world's population, lactose is poorly digested. Additionally, lactose has limited solubility in water resulting in undesirable crystallization in concentrated dairy foods. Since lactose has only one-fifth the degree of sweetness of sucrose, the use of whey concentrates or whey powder in processed foods has been limited.

Presently, β-galactosidase for food applications is available from various yeast and fungal sources. The enzymes that are used most extensively are those from *Kluyveromyces fragilis* and *Kluyveromyces lactis*. Unfortunately these enzymes do not tolerate the high temperatures used under industrial conditions.

BRIEF DESCRIPTION OF THE DRAWINGS

FIG. 2. Hydrolysis of lactose by ST1281(lacS−) mutant cells in PO buffer (pH 7.0) at 50° C. L=lactose. Data plotted represent averages of three replicate determinations.

SUMMARY OF THE INVENTION

Figure 1:
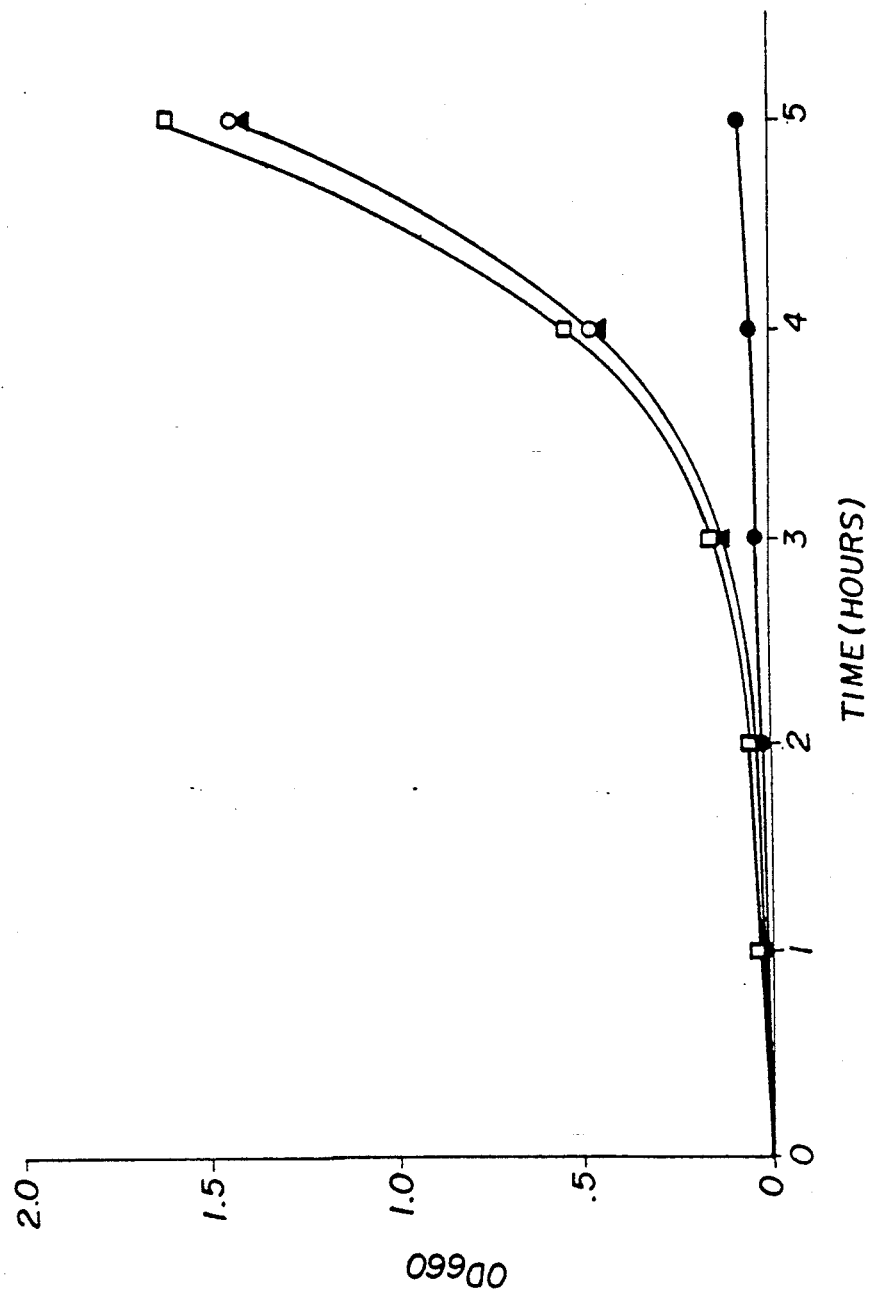
FIG. 1 Growth of wild-type *S. thermophilus* ST128 in glucose (●), lactose (○), and sucrose (▲) media, and growth of ST1281 (lacS−) in sucrose (□) medium. Incubation was at 37° C.

The relatively high thermostability of *S. thermophilus* makes this organism ideally suited for industrial applications. It is an object of the present invention to provide mutant strains of *S. thermophilus* having a defective lactose transport system. It is another object of the invention to provide methods for the efficient and economical production of reduced or lactose free dairy foods using these strains. When cells of the mutant strains are "decryptified", that is treated with solvent or detergent compositions, the resulting product act as "microcarriers" for thermostable β-galactosidase. These microcarriers can be stored for long periods without loss of enzyme activity. Addition of the microcarriers to lactose containing media results in hydrolysis without concomitant fermentation and the unwanted build up of lactic acid. Thermostability of the enzyme makes this product especially suited for industrial fermentation processes. Addition of the microcarriers prior to pasteurization to hydrolyze lactose may also decrease the time necessary to produce certain dairy products.

DETAILED DESCRIPTION OF THE INVENTION

Example 1

Organism and Culture Conditions

*S. thermophilus* ST128 was previously classified as a naturally galactose-negative (Gal−) strain (Somkuti, et al., J. Food Prot., Vol. 11, (1979), pp. 885-887). The culture was maintained in basal broth medium (BB) consisting of tryptone (Difco, 30 g/l), yeast extract (Difco, 10 g/l), beef extract (Difco, 2 g/l) and $KH_2PO_4$ (5 g/l) with a pH 6.5 before sterilization. The basal medium was supplemented with lactose (BBL), sucrose (BBS), glucose (BBG) or fructose (BBF), as required, at 5 g/l concentration. Incubation was at 37° C. for 24 h. Between weekly transfers, cultures were stored at 4° C.

Isolation of Lactose Transport System Defective (lacS−) Mutants

An overnight culture of *S. thermophilus* ST128 was transferred to fresh BBL medium and incubated at 37° C. until $OD_{660}=0.4$ was attained. Cells were pelleted by centrifugation at 10,000×g for 10 min at 4° C. and resuspended in 50 mM $K_2HPO_4$-$KH_2PO_4$ (pH 7.0) buffer (PO buffer) with 500 ug/ml N-methyl-N-nitroso-N'-nitroguanidine (NTG). After 60 min at room temperature, cells were washed twice with PO buffer and resuspended in peptone (Difco, 0.1 g/l) water.

Aliquots of serially diluted samples were plated in BBS medium with agar (Difco, 15 g/l). After 3 days at 37° C., 250 randomly selected colonies were patched on BBL and fresh BBS agar plates. LacS− mutants were scored after incubation for 48 h at 37° C. Mutation frequency was expressed as the number of lacS− colonies per surviving colony forming unit (CFU).

Growth Studies

The lacS− phenotype of lactose non-fermenting colonies that grew on BBS plates was verified by growth studies in BBL and BBS media. Isolates failing to show growth in BBL after 5 days were classified as having the lacS− phenotype. Possibility of reverse mutations to the lacS+ phenotype was checked routinely by plating BBS-grown cells on BBL agar.

Enzyme Assays

The β-galactosidase activity of lacS+ (wild type) and lacS− *S. thermophilus* was measured in decryptified cells treated with an acetone-toluene (AT) mixture as described by Somkuti and Steinberg, J. Appl. Biochem., Vol. 1, (1979), pp. 357-368 the disclosure of which is incorporated herein by reference. Activity was determined by measuring the amount of glucose released from 5% lactose in 50 mM PO buffer (pH 7.0) containing 1 mM $MgCl_2$. Reactions were carried out at 50° C. for 10 min. Glucose was determined spectrophotometrically with a Glucose Hexokinase (HK) Kit (Sigma Diagnostics, St. Louis Mo.) according to the manufacturer's recommendations. A unit of β-galactosidase activity was defined as the amount of enzyme that released 1 μmol of glucose per min. Protein was estimated by the method of Lowry, et al., J. Biol. Chem., Vol. 193, (1951), pp. 265-275 with bovine serum albumin as the standard. Viable cultures of the isolated lacS− *S. thermophilus* strain described above and useful in the present invention have been deposited with the Northern Regional Research Center, U.S. Department of Agriculture, Peoria, Ill. 61604 on Apr. 29, 1991, under the conditions set forth in the Budapest Treaty, and accorded the acquisition number NRRL 18818.

Lactose Hydrolysis by Entrapped lacS⁻ Cells

LacS⁻ phenotype cells from 2l of BBS medium following over night growth were centrifuged (10,000×g, 15 min, 4° C.), washed twice with PO buffer and finally resuspended in PO buffer for AT treatment. AT-treated cells were again washed twice before resuspension in PO buffer. Dry cell concentration of the suspension was 24 mg/ml (determined from a dry weight vs. $OD_{660}$ standard curve). Equal volumes (12 ml) of cell suspension and 3% agarose (FMC Bioproducts, Rockland, Me.) in PO buffer were mixed at 45° C. and poured on a 150×65 mm strip of GelBond firm (FMC Bioproducts).

Example 2

Mutation of S. thermophilus to lacS⁻ Phenotype

Treatment of S. thermophilus ST128 with NTG resulted in a 53% kill of the cell population under experimental conditions. Preliminary evaluation of clones on BBL and BBS agar plates indicated an apparent frequency of $10^{-1}$ for the lacS⁻ phenotype per surviving CFU. However, more exhaustive growth experiments with putative lacS⁻ mutants showed that some isolates grew in BBL very slowly, showing visible turbidity only after incubation for 96 h or longer at 37° C. Since these strains appeared only partially impaired in lactose transport, they were discarded.

Mutation affecting the lactose transport system led to the inability to ferment lactose. However, in lacS⁻ mutants high levels of cytoplasmic β-galactosidase may be synthesized (β-gal+), and other carbohydrate transport systems (e.g. sucrose, sucS+) may also be unimpaired. This appeared to be the case in several stringently selected (no growth in BBL) mutants of S. thermophilus ST128 which were lacS⁻, sucS+ and βgal+. The frequency of such mutants was $10^{-2}$ per surviving CFU following NTG treatment. The wild-type ST128 grew well in BBL and BBS, poorly in BBG and not at all in BBF. The lacS⁻ ST1281 grew exclusively in BBS (FIG. 1).

Enzyme analysis showed that β-galactosidase activity in ST1281(lacS⁻) (16 U per mg protein (Units are defined as micromoles/minute/mg protein)) was about 25% lower than in BBS-grown wild-type ST128 (21 U per mg protein). According to earlier data, β-galactosidase in S. thermophilus may be inducible (Somkuti, et al., J. Appl. Biochem., supra) or in some strains, constitutively expressed (Smart, et al., NZ J. Dairy Sci. Technol., Vol. 20, (1985), pp. 43-56). Results of this study indicated the presence of a constitutive β-galactosidase system in both wild-type ST128 and its mutant ST1281. The mutant strain appeared to be an excellent source of the enzyme.

Hydrolysis of Lactose by ST1281(lacS⁻)

Lactose hydrolysis was studied with cells of ST1281(lacS⁻) grown in BBS for 16 h at 37° C. Pelleted (10,000×g) and twice washed cells were resuspended in PO buffer at $OD_{660}=5.0$ for AT treatment at room temperature. After AT treatment cells were washed and resuspended at a final $OD_{660}=2.5$ in lactose solutions prepared at 5, 10, and 20% (wt/vol) concentrations in PO buffer. Reaction mixtures (5 ml) were held at 50° C. Aliquots were taken at appropriate intervals, cleared by centrifugation, dilutions made if needed, and multiples of 10-µl samples were assayed for glucose content. The results of these experiments are shown in FIG. 2. At low (5%) concentration which approximated the lactose content of cheese whey permeate from ultrafiltration, 83% of lactose was already hydrolyzed after 60 min and hydrolysis was nearly complete after 2 h incubation. At higher concentrations (10, 15 and 20%), the per cent lactose hydrolysed decreased progressively. This may have been caused by the increasing level of galactose, also accumulating in equimolar amounts in the reaction medium, which had been shown to be a weak competitive inhibitor of S. thermophilus β-galactosidase during lactose hydrolysis (Smart, et al., Appl. Microbiol. Biotechnol., Vol. 26, (1987), pp. 177-185).

The ST1281(lacS⁻) cells as microcarriers of β-galactosidase have excellent storage qualities. After storing decryptified cells in PO buffer for 4 months at 4° C., there was no detectable loss of β-galactosidase activity. These cells can be stored up to 1 yr or longer without significant loss of enzyme activity. The lacS⁻ phenotype appeared to be conserved in mutant cultures, and reversal to lacS+ resulting in growth on lactose was not observed after at least 100 transfers.

ST1281(lacS⁻) cells immobilized in 2.5-mm thick slabs of 1.5% agarose gel were also suitable for hydrolyzing lactose in aqueous solutions. The agarose gel strip was removed from the Gelbond support and placed in the shape of a cylinder in 200 ml 1% lactose (in PO buffer) in a beaker, and stirred magnetically at 45° C. As shown in Table 1, glucose accumulated rapidly in the reaction mixture and after 3 h, 92% of the lactose was hydrolyzed. Clearly, ST1281(lacS⁻) cells immobilized in agarose and other suitable entrapping materials (alginates, k-carrageenan, locust bean gum), also have potential applications in lactose hydrolysis.

TABLE 1

| Lactose Hydrolysis by Immobilized ST1281(lacS⁻) Cells | | |
|---|---|---|
| Time, min. | Glucose, mg/ml | % Lactose Hydrolysis |
| 0 | 0.008 | 0.1 |
| 30 | 2.18 | 41.4 |
| 60 | 3.26 | 62.0 |
| 90 | 3.83 | 72.7 |
| 120 | 4.43 | 84.2 |
| 150 | 4.68 | 88.9 |
| 180 | 4.86 | 92.2 |

Example 3

Hydrolysis of Lactose in Milk by lacS⁻ Mutants of S. thermophilus

Decryptified cells of lacS⁻ mutants of S. thermophilus prepared as described in Example 1 were condensed to yield a final $OD_{660}=5$ when resuspended in whole milk or skim milk. Reaction mixtures were held at 40° C. and samples were taken at predetermined time intervals to determine quantitatively the amount of glucose liberated from lactose as the result of β-galactosidase activity. The data shown in Table 2 indicates that after 3 h of incubation the per cent of lactose hydrolyzed nearly reached the maximum attainable level under the experimental conditions used.

TABLE 2

Lactose Hydrolysis in Milk by ST128(lacS⁻) Cells

| Time, hours | Per Cent of Lactose Hydrolyzed at 40° C. | |
|---|---|---|
| | Whole Milk | Skim Milk |
| 0 | 0.1 | 0.1 |
| 1 | 54.1 | 44.0 |
| 2 | 72.3 | 66.0 |
| 3 | 77.1 | 77.5 |
| 4 | 81.0 | 77.5 |
| 5 | 80.0 | 79.3 |

Example 4

Hydrolysis of Lactose in Milk by Entrapped lacS⁻ Mutants of *S. thermophilus*

Decryptified cells of lacS⁻ mutants of *S. thermophilus* were prepared and entrapped in 1.5% agarose matrix as described in Example 1. A 6.5 cm×15.0 cm slab of the agarose slab was suspended in 200 ml of skim milk and the mixture was stirred magnetically with a stirring bar at 45° C. Samples were taken at predetermined time intervals to determine quantitatively the amount of glucose liberated from lactose as the result of β-galactosidase activity. The data shown in Table 3 indicates that after 5 h of incubation 95 per cent of the lactose was hydrolyzed to its constituent monosaccharides, glucose and galactose.

TABLE 3

Lactose Hydrolysis in Milk by ST128(lacS⁻) Cells Entrapped in Agarose

| Time, hours | Per Cent of Lactose Hydrolyzed in Skim Milk at 45° C. |
|---|---|
| 0 | 0 |
| 0.5 | 21.0 |
| 1 | 36.5 |
| 2 | 65.6 |
| 3 | 82.2 |
| 4 | 89.6 |
| 5 | 95.4 |

Example 5

Industrial Bioprocessing

The decryptified cells of Example 2 can serve well in bioprocessing technology. The cells act as biocatalysts and can be used immobilized or free. Immobilization can be accomplished by entrapment in which the cells are incorporated into a polymer matrix that traps them while allowing free passage of water and low molecular weight solutes. Microencapsulation provides for the incorporation of cells into small semipermeable membrane microcapsules. These microcapsules also allow the free exchange of water and solutes to and from the cells. These microcapsules then provide utility for both packed and fluidized-bed reactors.

It is envisioned that immobilization of free enzyme or whole cells can be effected using any one of several techniques known in the art such as adsorption in which the enzyme or whole decryptified cells adhere loosely, absent a chemical bond, to the surface of a solid support material. Chemical bonding can be used to attach free enzyme or cells to a solid support either directly or using a linker.

It can be seen that the use of lactose transport defective (lacS⁻) mutants of *S. thermophilus* have distinct advantages in commercial lactose hydrolysis. These food-grade enzyme microcarriers with high levels of constitutive β-galactosidase activity may be grown in inexpensive sucrose-based media. Since they cannot ferment lactose or glucose to lactic acid, they do not contribute to the acidification of foods, making the isolation of β-galactosidase from the cells unnecessary. Lactose nonfermenting cultures treated appropriately (solvents and/or detergents) to express maximum enzyme activity and washed free of treatment formulations may be added directly to food systems to reduce lactose content or used in large-scale lactose hydrolysis.

Thus it can be seen there has been provided in accordance with the present invention, a mutant strain of *Streptococcus thermophilus* having a defective lactose transport system and methods for its use in the hydrolysis of lactose and the preparation of dairy products.

The invention as described by the specific embodiments is not meant to limit its scope. It is envisioned and apparent that many alternatives and variations may be encompassed by the present invention. It is intended that the spirit and scope of this disclosure include such alternatives and variations.

I claim:

1. A biologically pure culture of *Streptococcus thermophilus* having a phenotype comprising lacS⁻, gluS⁻, sucS⁺ and βgal⁺.

2. The biologically pure culture of claim 1, wherein the culture is *S. thermophilus* NRRL 18818.

3. The biologically pure culture of claim 1, in which cells of the culture are decryptified.

* * * * *